United States Patent
Stempfer et al.

(10) Patent No.: US 8,426,168 B2
(45) Date of Patent: Apr. 23, 2013

(54) PROCESS FOR THE PREPARATION OF RECOMBINANT POLYPEPTIDES

(75) Inventors: Günter Stempfer, Kufstein (AT); Norbert Palma, Breitenbach a. Inn (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/568,329

(22) PCT Filed: Aug. 19, 2004

(86) PCT No.: PCT/EP2004/009321
§ 371 (c)(1),
(2), (4) Date: Feb. 15, 2006

(87) PCT Pub. No.: WO2005/019466
PCT Pub. Date: Mar. 3, 2005

(65) Prior Publication Data
US 2006/0269990 A1    Nov. 30, 2006

(30) Foreign Application Priority Data
Aug. 20, 2003  (GB) ................... 0319601.1

(51) Int. Cl.
*C12P 21/04*  (2006.01)
*C12N 15/74*  (2006.01)
*A01N 63/00*  (2006.01)

(52) U.S. Cl.
USPC .......................... 435/71.2; 435/471

(58) Field of Classification Search .................. None
See application file for complete search history.

(56) References Cited

U.S. PATENT DOCUMENTS

| | | | |
|---|---|---|---|
| 6,337,205 B1 * | 1/2002 | Wisniewski | 435/307.1 |
| 6,613,335 B1 * | 9/2003 | Ruelle | 424/251.1 |
| 7,033,798 B2 * | 4/2006 | Pluckthun et al. | 435/69.6 |

OTHER PUBLICATIONS

Mendonca et al Destruction of Gram-negative Food-Borne Pathogens by High pH involves disruption of the cytoplasmic membrane. Applied and Environmental Microbiology 60:4009-4014, 1994.*
Jordan et al. Survival of Low-pH stress by *Escherichia coli* O157:H7: Correlation between alterations in the cell envelope and increased acid tolerance. Applied and Environmental Microbiology 65:3048-3055, 1999.*
Donovan et al. Review: Optimizing Inducer and Culture Conditions for Expression of Foreign Proteins Under the Control of the lac Promoter, by RS Donovan, CW Robision and BR Glick, Journal of Industrial Microbiology (1996), pp. 145-154.

* cited by examiner

*Primary Examiner* — Quang Nguyen
(74) *Attorney, Agent, or Firm* — Luedeka Neely Group, P.C.

(57) ABSTRACT

The present invention relates to the preparation of a recombinant polypeptide, which polypeptide upon expression has been secreted into the periplasm of a transformed host cell. In particular, this invention relates to a process to enhance the extraction yield of the recombinant polypeptide from the periplasm before further downstream processing.

12 Claims, No Drawings

PROCESS FOR THE PREPARATION OF RECOMBINANT POLYPEPTIDES

This application is a national stage application of copending PCT International Application No. PCT/EP2004/009321, filed Aug. 19, 2004. This application also claims the benefit of the filing date of British patent application No. 0319601.1, filed Aug. 20, 2003.

FIELD OF THE INVENTION

The present invention relates to the preparation of a recombinant polypeptide, which polypeptide upon expression has been secreted into the periplasm of a transformed host cell. In particular, this invention relates to a process to enhance the extraction yield of said recombinant polypeptide from the periplasm before further downstream processing.

BACKGROUND OF THE INVENTION

Polypeptides or proteins may be made by recombinant DNA technology using bacterial cells (e.g. *Escherichia coli*) as hosts. Thus, bacterial cells may be transformed with plasmid DNA encoding said polypeptide or protein. The bacteria are thereby enabled to express quantities of the polypeptide in either the cytoplasm, or the periplasm or the extracellular space. As the bacteria can be grown in large amounts using large-scale fermentation processes, it is possible to produce large quantities of the polypeptide in this way.

Secretion of polypeptides or proteins into the periplasm has a number of potential advantages, including separation from cytoplasmic proteins, particularly proteases, avoidance of cytoplasmic toxicity, avoidance of N-terminal methionine extension, and accumulation in a more oxidizing environment where disulfide-bond formation may proceed and the protein may fold into a soluble, biologically active confirmation. Superficially, it requires only that the desired protein be fused to a signal peptide (secretory leader) at its N-Terminus although, the efficiency of secretion is likely also influenced by structural features of the protein, as well as its usual location within the cell.

*E. coli* is well-equipped to secrete proteins through the cytoplasmic membrane into the periplasm, and this approach has been used widely to direct heterologous proteins out of the cell cytoplasm. It has been particularly successful in enabling the production of biologically active antibody fragments and this approach now challenges the production of whole antibodies in animal cell culture.

Secretion of heterologous proteins is rarely 100% efficient and, in several cases, unprocessed precursor protein with the secretory leader attached accumulates within the cell. This observation suggests that one or more components of the secretory apparatus can limit the export of these proteins.

One notable feature of the literature on protein secretion in *E. coli* is the frequency of reports in which the protein is recovered directly from the growth medium. This can be highly advantageous, but raises unresolved questions about the underlying mechanisms. There are reports showing that proteins are often released into the medium by non specific leakage from, or lysis of, the cell, and not by specific translocation through the outer membrane. This phenomenon is not understood and is highly protein-sequence specific, being extensive with some antibody fragments and insignificant with other polypeptides.

Secretion of proteins into the periplasm is a useful route and can lead to the rapid isolation of a protein for biological evaluation. Its application on industrial scale is currently limited by the general unavailability of efficient, scaleable methods for selective release of periplasmic proteins from the cell.

If the recovery of a recombinant protein from the periplasm can be achieved without contamination by cytoplasmic proteins, subsequent purification steps are simplified very much, since, for instance in *E. coli*, only 7 out of the 25 known cellular proteases and about 4-8% of the total cell protein are located in the periplasm (Swamy et al., Baneyx et al.).

There are various frequently used methods for selective release of periplasmic proteins. One is cell permeabilization involving chemicals such as chloroform, guanidine-HCl, Cetyl-trimethyl-ammonium-bromide/CTAB or detergents such as Triton X-100 and glycine. Others are permealization using lysozyme/EDTA treatment or application of osmotic shock. These release methods are suitable also for large scale preparation and have been used in many different modifications on a wide range of expression systems with varying degrees of success.

The state of the art methodology on periplasmic release of proteins is documented for example in the following literature:

Swamy et al., J. Bacteriol. 147, 1027-1033, 1982
Baneyx et al., J. Bacteriol. 173, 2696-2703, 1991
Blight et al., TibTech 12, 450-455, 1994
Barbero et al., Journal of Biotechnology 4, 255-267, 1986
Pierce et al., Journal of Biotechnology 58, 1-11, 1997
French et al., Enzyme & Microbial Technology 19, 332-338, 1996
Naglak et al., Enzyme & Microbial Technology 12, 603-611, 1990
Nossal et al., J. Biol. Chem 241 (13), 3055-3062, 1966
Neu et al., J. Biol. Chem 240, 3685-3692, 1965
Hsiung et al., Bib/Technology 4, 991-995, 1986
Carter et al., Bio/Technology 10, 163-167, 1992
Georgiou et al., Biotechnol. Bioeng. 32, 741-748, 1988
Aristidou et al., Biotechnolgy Letters 15 (4), 331-336, 1993
Chaib et al., Biotechnology Techniques 9 (3), 179-184, 1195
Ames et al., J. Bacteriol. 160, 1181-1183, 1984
Gellerfors et al., J. Pharm. Biomed. Anal. 7, 2, 173-83, 1989
Chapman et al, Nature Biotechnology 17, 780-783, 1999
Voss et al., Biochem. J. 298, 719-725, 1994
WO 01/94585
U.S. Pat. No. 4,845,032
U.S. Pat. No. 4,315,852

Whereas recombinant techniques can be employed to produce high yields of a crude polypeptide, the isolation and purification of the polypeptide requires sophisticated and extensive procedures.

In a typical isolation procedure, the fermentation harvest broth is adjusted to a neutral pH (e.g pH 6.5-7.5) by addition of acid or caustic. Thereafter, the bacterial cells are removed e.g. by centrifugation or microfiltration to leave a liquid supernatant, containing unwanted soluble by-products, which is discarded. The resultant bacterial cell mass is resuspended in an appropriate medium, e.g. a suitable buffer, and the cells are disrupted to extract and isolate the product.

Laborious extraction and isolation procedures are usually carried out in order to separate the polypeptide of interest from as much fermentation by-products and other contaminants as possible to ensure that subsequent purification steps proceed in an as efficient manner as possible.

Purification steps known in the art generally comprise precipitation and chromatographic separation techniques, and sometimes require additional steps like diafiltration and/or concentration procedures, which are laborious and may lead to lower yields of extracted polypeptide and higher production costs.

The extraction, isolation and purification of a polypeptide implicates losses of material or biological activity at every stage of the process.

Proteolysis, i.e. degradation of the polypeptides by proteolytic enzymes, usually occurring after disruption of the bacterial cells, but also observed in vivo, is considered to be one of the main causes of protein loss. This adventitious proteolysis is a technical problem which requires modifications of the methodology to minimize the degradation of the polypeptide of interest.

One way of keeping the rate of proteolysis low, is generally to perform the harvest, extraction, isolation and purification procedures at reasonably low temperatures and as fast as possible. Accordingly, relevant text books and standard protocols on isolation and purification of polypeptides in general teach to proceed without unnecessary delays and interruptions (Protein Protocols, Ed. J. M. Walker, Humana Press Inc., January 1998).

Accordingly, there is a need for novel processes that enable the extraction of recombinant polypeptides of interest from bacterial cells in a high yielding and cost-effective manner.

The present invention complies with the above mentioned needs by providing novel methods for the preparation of recombinant polypeptides.

In the context of the present invention it has surprisingly been found that the yield of a recombinant polypeptide expressed in a bacterial host comprising a periplasm can be increased by interrupting the isolation process after fermentation and put on hold the further processing of the fermentation harvest broth before the subsequent steps of extraction and isolation of said polypeptide are performed.

SUMMARY OF THE INVENTION

The present invention relates to a process for the preparation of a recombinant polypeptide, comprising the steps of
a) fermenting a prokaryotic host cell comprising a periplasm and being transformed with a recombinant expression system capable of effecting secretion of the polypeptide into the periplasm, which fermentation is performed in a fermentation medium under conditions such that the polypeptide is secreted into the periplasm of the host cell, and
b) interrupting the further processing of the fermentation harvest broth and maintaining it under defined conditions of temperature and pH prior to extraction.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

All patent applications, patents and literature references cited herein are hereby incorporated by reference in their entirety.

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes 1 and 11, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

The present invention relates to a process for the preparation of a recombinant polypeptide, comprising the steps of
a) fermenting a prokaryotic host cell comprising a periplasm and being transformed with a recombinant expression system capable of effecting secretion of the polypeptide into the periplasm, which fermentation is performed in a fermentation medium under conditions such that the polypeptide is secreted into the periplasm of the host cell, and
b) interrupting the further processing of the fermentation harvest broth and maintaining it under defined conditions of temperature and pH prior to extraction.

The invention is based on the surprising finding that the yield of a recombinant polypeptide expressed in a bacterial host comprising a periplasm can be increased by interrupting the isolation process after fermentation and put on hold the further processing of the fermentation harvest broth before the subsequent steps of extraction and isolation of said polypeptide are performed.

The expression of the polypeptide is performed in a suitable prokaryotic host cell comprising a periplasm and being transformed with a recombinant expression system capable of effecting secretion of the polypeptide into the periplasm (described e.g. in Skerra and Plickthun, Science 240, 1038-1041, 1988).

The fermentation of the polypeptide is performed in a fermentation medium under appropriate conditions such that the polypeptide is secreted into the periplasm of the host cell (described e.g. in Skerra and Plückthun, Science 240, 1038-1041, 1988).

As used herein, the term "fermentation" is understood to mean growing a host cell in an appropriate fermentation medium for an appropriate period of time under appropriate conditions such that the polypeptide is produced by the host cell and secreted into the periplasm.

Said interruption of the further processing may be accomplished, for example, by maintaining, retaining, keeping or storing the fermentation harvest broth for at least one hour under appropriate conditions which ensure as far as possible the integrity of the produced polypeptide, i.e. that it is not degraded or otherwise impaired in function or structure. This can be achieved, for instance, by maintaining, retaining, keeping or storing the fermentation harvest broth either directly in the fermentation tank (fermenter), or transferring said fermentation harvest broth into another tank or any other suitable container after collection from the fermenter. Furthermore, the fermentation harvest broth may be stirred periodically or continuously during the interruption step.

Accordingly, in a preferred embodiment, step b) of the above process is performed in the fermenter.

Usually, with regard to the desired increase of product yield, there will be a relationship between the duration of the interruption step and the temperature applied. A low temperature will require a longer time period whereas at a higher temperature a shorter time period will be sufficient in order to achieve similar results. The optimal parameters are dependent on the expressed polypeptide, the host cell and the production conditions.

Accordingly, in a preferred embodiment, a process for the preparation of a recombinant polypeptide is provided, wherein the further processing of the fermentation harvest broth is interrupted for a period of at least about one hour, e.g. for a period of one hour.

Preferably, the further processing of the fermentation harvest broth is interrupted for a period of about one hour to about 72 hours, e.g. for a period of one hour to 72 hours. Further processing may be interrupted for any period within this range.

More preferably, the further processing of the fermentation harvest broth is interrupted for a period of about 12 hours to about 48 hours, e.g. for a period of 12 hours to 48 hours. Further processing may be interrupted for any period within this range.

Most preferably, the further processing of the fermentation harvest broth is interrupted for a period of about 12 hours, about 24 hours or about 48 hours., e.g. for a period of 12 hours, 24 hours or 48 hours.

In a further preferred embodiment, a process for the preparation of a recombinant polypeptide is provided, wherein the interruption of the further processing of the fermentation harvest broth is performed at a temperature of about 2° C. to about 65° C., e.g. at a temperature of 2° C. to 65° C. Further processing may be interrupted at any temperature within this range.

More preferably, further processing of the fermentation harvest broth is interrupted at a temperature of about 4° C. to about 25° C., e.g. at a temperature of 4° C. to 25° C. Further processing may be interrupted at any temperature within this range.

Most preferably, further processing of the fermentation harvest broth is interrupted at a temperature of about 4° C., about 10° C., about 15° C., about 20° C. or about 25° C., e.g. at a temperature of 4° C., 10° C., 1-5° C., 20° C. or 25° C.

In a further preferred embodiment, a process for the preparation of a recombinant polypeptide is provided, wherein further processing of the fermentation harvest broth is interrupted for a period of about 12 hours, about 24 hours or about 48 hours at a temperature of about 4° C., about 10° C., about 15° C., about 20° C. or about 25° C., e.g. for a period of 12 hours, 24 hours or 48 hours at a temperature of 4° C., 1.0° C., 15° C., 20° C. or 25° C.

In another preferred embodiment, a process for the preparation of a recombinant polypeptide is provided, wherein the pH value of the fermentation harvest broth is maintained between about 4 to about 10 during step b), e.g. between 4 to 10. The fermentation harvest broth may be maintained at any pH value within this range.

More preferably, the pH value of the fermentation harvest broth is maintained between about 5 to about 9 during step b), e.g. between 5 to 9. The fermentation harvest broth may be maintained at any pH value within this range.

Even more preferably, the pH value of the fermentation harvest broth is maintained between about 6 to about 8 during step b), e.g. between 6 to 8. The fermentation harvest broth may be maintained at any pH value within this range.

Most preferably, the pH value of the fermentation harvest broth is maintained at about 7, e.g. at 7 during step b).

In practising the present invention it is not necessary to stick to exact values of temperature, pH and time, i.e. with respect to the above embodiments said values are to be understood as approximate or mean values. The present invention is workable within a broad range of conditions and allows some variation. A skilled person will know that some variation around given values is possible and in practice sometimes even unavoidable. Hence, during the interruption step period e.g. the preset pH value may change slightly and may be readjusted as appropriate or necessary. Also the applied temperature may vary to some extent, e.g. when the interruption step is performed by incubating the fermentation harvest broth in a cold storage room. In such a cold storage room the preset temperature normally varies within a certain tolerable range, e.g. from 2° C. to 8° C. with an average mean value of e.g. 4° C. or 5° C. over a certain time period. Therefore, within the context of the present invention, a given pH of e.g. 4 or a given temperature of e.g. 25° C. does not mean an exact pH of 4.0 or an exact temperature of 25.0° C.

Before starting the interruption period, the appropriate conditions such as, for instance, suitable temperature and pH of the fermentation harvest broth are adjusted according to requirements determined by the expressed polypeptide. The most suitable conditions for a specific polypeptide will be either known or can be easily determined applying standard methods known in the art (Protein Protocols, Ed. J. M. Walker, Humana Press Inc., January 1998).

After the interruption period the fermentation harvest broth usually will be extracted in order to isolate the recombinant polypeptide and separate it from cellular material and unwanted fermentation by-products. Frequently used methods for selective release of periplasmic proteins are among others lysozyme and/or EDTA treatment optionally followed by osmotic shock treatment or any other suitable release procedure like pH or temperature incubation for a specified time period.

In the context of the present invention it is to be understood that step b) of the above process does not have to be necessarily performed directly following step a). Additional process steps may be performed between step a) and b). For instance, a partial extraction of the fermentation harvest broth prior to the application of the interruption period is encompassed by the present invention. As long as not the complete fermentation harvest broth is further processed, the interruption period will result in an increased polypeptide yield.

In addition, the fermentation harvest broth may be washed and/or concentrated in order to reduce the volume of the material and simplify its further processing, e.g. by centrifugation using a disk stack separator, microfiltration, flocculation and sedimentation or by precipitation and filtration, resulting in a wet cell paste. The extent of concentration may vary from partially reducing the volume for just a small percentage to the maximum possible or appropriate, which may e.g. be determined by the desired final consistency in terms of percent of wet weight. The concentration of the fermentation harvest broth may be done before or after the interruption step, but preferably is done before.

Therefore, in a preferred embodiment, a process for the preparation of a recombinant polypeptide is provided, comprising the steps of a) fermenting a prokaryotic host cell comprising a periplasm and being transformed with a recombinant expression system capable of effecting secretion of the polypeptide into the periplasm, which fermentation is performed in a fermentation medium under conditions such that the polypeptide is secreted into the periplasm of the host cell, and b) interrupting the further processing of the fermentation harvest broth and maintaining it under defined conditions of temperature and pH prior to extraction, and
wherein the fermentation harvest broth is concentrated prior to step b).

Preferably, the fermentation harvest broth is concentrated by centrifugation or microfiltration prior to step b).

A number of prokaryotic host cells comprising a periplasm may be used to practice the present invention.

Accordingly, in a preferred embodiment, a process for the preparation of a recombinant polypeptide is provided, comprising the steps of
a) fermenting a prokaryotic host cell comprising a periplasm and being transformed with a recombinant expression system capable of effecting secretion of the polypeptide into the periplasm, which fermentation is performed in a fermentation medium under conditions such that the polypeptide is secreted into the periplasm of the host cell, and
b) interrupting the further processing of the fermentation harvest broth and maintaining it under defined conditions of temperature and pH prior to extraction, and
wherein the prokaryotic host cell is a Gram-negative bacterium.

More preferably, the Gram-negative bacterium is selected from the group consisting of *Escherichia* sp., *Pseudomonas* sp., *Enterobacter* sp., *Erwinia* sp., *Campylobacter* sp., *Proteus* sp., *Aeromonas* sp. and *Vitreoscilla* sp.

Most preferred is the use of *Escherichia coli*. Particularly suitable *E. coli* strains are *E. coli* K and B strains such as e.g. *E. coli* K12 or *E. coli* BL21.

The process of the present invention is broadly applicable and is not limited to the preparation of particular recombinant polypeptides or proteins.

However, in a preferred embodiment, the present invention provides a process for the preparation of a recombinant polypeptide, comprising the steps of
a) fermenting a prokaryotic host cell comprising a periplasm and being transformed with a recombinant expression system capable of effecting secretion of the polypeptide into the periplasm, which fermentation is performed in a fermentation medium under conditions such that the polypeptide is secreted into the periplasm of the host cell, and
b) interrupting the further processing of the fermentation harvest broth and maintaining it under defined conditions of temperature and pH prior to extraction, and
wherein the recombinant polypeptide is an antibody, a hormone or an immunomodulating agent.

More preferably, the recombinant polypeptide is a growth hormone, a growth factor, an interferon, a cytokine, an enzyme, an enzyme inhibitor or an antibody fragment.

Most preferably, the recombinant polypeptide is a Fab-fragment, human growth hormone, interferon alpha-2b or granulocyte colony-stimulating factor.

The invention is further described by reference to the following examples. These examples are provided for illustration purposes and are not intended to be limiting.

EXAMPLES

In the Examples the following abbreviations are used:

| | |
|---|---|
| aa = | amino acid |
| A = | peak area |
| AEX = | anion exchange chromatography |
| BH = | bed height |
| C = | conductivity (mS/cm) |
| CAP.P = | capture pool |
| CE = | clarified crude extract |
| CP = | pellet after centrifugation |
| CR = | cell resuspension |
| CV = | column volume |
| DBE = | direct broth extraction |
| DR = | diaretentate |
| DSP = | down stream processing |
| EBA = | expanded bed adsorption |
| EXT = | extraction |
| Fab' = | antibody Fab' fragment |
| GAC = | Glutaryl-7-ACA-Acylase |
| HB = | harvest broth |
| HCP = | host cell proteins |
| HG = | homogenate |
| HIC = | hydrophobic interaction chromatography |
| IPC = | In Process Controls |
| MBR = | Master Batch Record |
| MF = | microfiltration |
| N = | theoretical plates |
| p = | pressure (bar) |
| P = | protein |
| PCM = | packed cell mass |
| PEI = | polyethyleneimine |
| PS = | primary separation |
| (a)RPC = | (acid) reversed phase chromatography |
| rpm = | rounds per minute |
| Rs = | resolution |
| SDS-PAGE = | sodium dodecylsulfate polyacrylamide gel electrophoresis |
| SEC = | size exclusion chromatography |
| ss = | stainless steel |
| T = | temperature (° C.) |
| t = | time (h) |
| TMP = | transmembrane pressure |
| UF/DF = | ultrafiltration/diafiltration |
| V = | volume (L) |
| W = | weight (kg) |
| wBM = | wet biomass (= BFM) |
| WBR = | purified water |
| WFI = | water for injection |

Example 1

Periplasmic Expression of an Antibody Fab'-Fragment (Fab')

The light and heavy chain of a humanized antibody Fab'-fragment having specificity for human tumor necrosis factor-alpha (disclosed in WO 01/94585) is cloned and expressed in *E. coli* K12. A vector is used enabling the sequential expression of light and heavy chain each as N-terminal fusions with a signal sequence under common control of a suitable promoter.

After fermentation of the humanized Fab'-producing *E. coli* K12 strain, the harvest broth is clarified by centrifugation (Wesffalia CSC6 disk separator), 100 Uh, 15000×g, then the isolated cell paste resuspended immediately or after a specified interruption period (time, temperature, wet weight consistency) with extraction buffer (200 mM Tris/HCl pH 7.4, 20 mM EDTA) to the original harvest volume (final concentration 100 mM Tris/HCl, 10 mM EDTA) and each preparation extracted 30 min at 25° C. After the 30 min extraction an analytical aliquot of each cell suspension preparation is clarified immediately by centrifugation (Beckman Avanti J25 I, Rotor 25.5, 20.000×g) plus 0.2 μm filtration (PALL Acrodisc 32 syringe 0.2 μm filter). All clarified extracts are analysed for Fab' (aRPC) and total protein content (Bradford).

The results in table 1 show that the Fab' extraction yield can be increased by including an interruption step after clarification and prior to extraction.

TABLE 1

| | Interruption step | | Relative extraction yield |
|---|---|---|---|
| Sample | h | ° C. | % |
| 1 | 0 | — | 100 |
| 2 | 24 | 4 | 168 |
| 3 | 48 | 4 | 203 |
| 4 | 24 | 25 | 451 |
| 5 | 48 | 25 | 621 |

Example 2

Periplasmic Expression of Recombinant Human Growth Hormone (rhGH)

The structural gene of human growth hormone is cloned and expressed in *E. coli* K12 using a vector enabling the expression of rhGH as an N-terminal fusion protein with a signal sequence under control of a suitable promoter. The signal sequence is cleaved during the export into the periplasmic space of the host cell leaving a native polypeptide sequence in the periplasm.

After fed batch fermentation, the rhGH-containing *E. coli* harvest broth is adjusted to pH 5 with sulfuric acid and immediately cooled down to 5-15° C. The low pH as well as the low temperature help to inactivate endogenous proteases and aminopeptidases. Then the treated harvest broth is concentrated to about half of the original volume by subsequent centrifugation (Wesffalia separator CSC6, 200 L/h, 15000×g) or microfiltration (MF, 0.2 μm Hydrosart/Sartorius, TMP about 1 bar) and subsequently washed with process water until a final conductivity of 3-5 mS/cm.

Without or after a specified interruption step (24 hours or 48 hours at 4° C. or 20° C.) the concentrated cell paste and the harvest broth itself (DBE without prior concentration/washing step) are conditioned with sucrose/EDTA stock solution to reach a final concentration of 1 mM EDTA, 200 g/L sucrose and about 10-20% wet cell weight. After one hour incubation by gentle stirring at 2-8° C. the conditioned cell suspension is diluted into cold water (osmotic shock by 1+4 dilution) and the incubation continued for an additional hour. After this osmotic shock polyethyleneimine (Polyethyleneimine 50%, BASF) is added to a final concentration of 0.05% and the pH adjusted to 7.5 with sulfuric acid. Subsequent centrifugation (Wesffalia separator CSC6) and filtration (0.3 μm Polygard plus 0.2 μm Durapore/Millipore) gives a clear protein solution with 0.1-0.3 mg rhGH/mL with a purity of >20% in respect to total Bradford protein.

The rhGH containing extract is then adjusted to a final conductivity of 3-5 mS/cm (or by dilution or by diafiltration over a 5-10 kD Biomax membrane, Millipore) and captured by anion exchange chromatography (Q-HyperD ° F., Biosepra, load capacity >50 mg total protein/ml packed resin, linear flow 3-5 cm/min, bed height 10-20 cm).

The rhGH extraction yield can be increased by including an interruption step after fermentation/clarification and prior to extraction.

Example 3

Periplasmic Expression of Recombinant Human Interferon Alpha-2B (rhIFN α-2B)

rhIFN α-2B is produced by fermentation of the recombinant *E. coli* K12 W3110 strain under the control of the Pgac promoter. The target protein is expressed as N-terminal fusion with the signal peptide of the bacterial Glutaryl-ACA-Acylase (GAC) from *Pseudomonas diminuta* CCM 3987 (described in CS 278515, CS 260068).

As in example 2 the harvest broth is initially washed with process water at constant volume and then concentrated by subsequent centrifugation (Wesffalia separator CSC6, 200 L/h, 15000×g) or microfiltration (MF, 0.2 μm Hydrosart/Sartorius, TMP about 1 bar) until a final conductivity of about 4 (range 3-5) mS/cm and a final consistency of 45±5% wet weight. Further processing is performed with or without a subsequent interruption step, i.e. with or without maintaining the concentrated cell paste or the harvest broth itself (DBE without prior concentration/washing step) for 24 or 48 hours at a temperature of 4° C. or 20° C. Afterwards, an EDTA/sucrose stock solution is added to the washed cell paste or harvest broth to reach a final concentration of 10 mM EDTA, 200 g/L sucrose and 10-20% wet cell weight, and the slurry is adjusted to pH 8.0 with NaOH. After one hour incubation by gentle stirring at 2-8° C. the conditioned cell suspension is diluted into cold water (osmotic shock by 1+4 dilution) and the incubation continued for an additional hour, then clarified similar as in the rhGH experiment (example 2) via Polyethylene-imine flocculation and subsequent centrifugation and filtration resulting in a clear protein solution with approximately 0.005-0.025 mg rhIFN α-2B per mL extract (estimated by densitometric SDS-PAGE plus Western detection). For product capture the clear extract is adjusted to 3.5-4.5 mS/cm (or by dilution or by diafiltration over a 5-10 kD Biomax membrane, Millipore), adjusted to pH 5 with diluted $CH_3COOH$ and loaded on an equilibrated S Ceramic HyperD F column (S Ceramic HyperD F, Biosepra, load capacity 30-70 mg protein/ml resin, 2-6 cm/min, EQ-buffer 20 mM Na-acetate+70 mM NaCL pH 5.0). After a washing step with equilibration buffer the rhIFN α-2B is eluted with approximately 2 CV elution buffer (20 mM Na-acetate+175 mM NaCL pH 5.0). In the capture pool the target protein is quantified by aRPC and the purity estimated by product content versus total protein measured with the Bradford method.

The rhIFN α-2B extraction yield can be increased by including an interruption step after fermentation/clarification and prior to extraction.

What is claimed is:

1. A process for the preparation of a recombinant polypeptide, consisting essentially of the steps of
    a) fermenting a prokaryotic host cell in a fermentation medium, the host cell comprising a periplasm and being transformed with a recombinant expression system capable of effecting secretion of the polypeptide into the periplasm of the host cell, wherein the fermentation is performed in the fermentation medium under conditions such that polypeptide is secreted into the periplasm of the host cell,
    b) interrupting further processing of the host cell by maintaining, retaining, keeping, or storing the fermentation harvest broth under non-lethal conditions at a temperature of from about 4° C. to about 25° C. at a pH of from about 4 to about 10 and for a time ranging from at least 1 hour to about 72 hours so as to ensure that the integrity of polypeptide secreted into the cell periplasm in the cell in the fermentation harvest broth is maintained while avoiding any further fermentation of the medium;
    c) concentrating the fermentation harvest broth by centrifugation or micro filtration either prior to or after interruption of the further processing in step b), and
    d) recovering polypeptide from cell periplasm in the concentrated fermentation harvest broth following interruption of further processing of the fermentation harvest broth in step b), wherein the yield of polypeptide recovered from the periplasm is increased compared to the polypeptide yield of processes in which further processing is not interrupted.

2. The process according to claim 1, wherein the pH of the fermentation harvest broth is maintained at a pH ranging from about 5 to about 9 during step b).

3. The process according to claim 1, wherein the pH of the fermentation harvest broth is maintained at a pH ranging from about 6 to about 8 during step b).

4. The process according to claim 1, wherein the pH of the fermentation harvest broth is maintained at about 7 during step b).

5. The process according to claim 1, wherein step b) is performed in a fermenter.

6. The process according to claim 1, wherein the prokaryotic host cell comprises a Gram-negative bacterium.

7. The process according to claim 6, wherein the Gram-negative bacterium is selected from the group consisting of *Escherichia* sp., *Pseudomonas* sp., *Enterobacter* sp., *Erwinia* sp., *Campylobacter* sp., *Proteus* sp., *Aeromonas* sp. and *Vitreoscilla* sp.

8. The process according to claim 6, wherein the Gram-negative bacterium comprises *Escherichia coli*.

9. The process according to claim 1, wherein the recombinant polypeptide is selected from the group consisting of an antibody, a hormone, and an immunomodulating agent.

10. The process according to claim 1, wherein the recombinant polypeptide is selected from the group consisting of a growth hormone, a growth factor, an interferon, a cytokine, an enzyme, an enzyme inhibitor, and an antibody fragment.

11. The process according to claim 1, wherein the recombinant polypeptide is selected from the group consisting of a Fab-fragment, human growth hormone, interferon alpha-2b, and granulocyte colony-stimulating factor.

12. The process according to claim 1, wherein the further processing of the fermentation harvest broth is interrupted for a period of about 12 hours to about 48 hours.

* * * * *